US005789607A

United States Patent [19]
Okabe

[11] Patent Number: 5,789,607
[45] Date of Patent: Aug. 4, 1998

[54] PROCESS FOR THE PREPARATION OF 1,25-DIHYDROXY-16-ENE-23-YNE-CHOLECALCIFEROL

[75] Inventor: Masami Okabe, Nutley, N.J.

[73] Assignee: Hoffmann-La Roche Inc., Nutley, N.J.

[21] Appl. No.: 844,008

[22] Filed: Apr. 18, 1997

Related U.S. Application Data

[63] Continuation of Ser. No. 356,942, Dec. 15, 1994, abandoned, which is a continuation of Ser. No. 192,665, Feb. 7, 1994, abandoned.

[51] Int. Cl.[6] .................................................. C07J 9/00
[52] U.S. Cl. ........................................................ 552/505
[58] Field of Search ............................... 552/505, 541, 552/653; 514/167

[56] References Cited

U.S. PATENT DOCUMENTS

| | | |
|---|---|---|
| 3,970,676 | 7/1976 | Salmond . |
| 4,011,250 | 3/1977 | Ishikawa et al. . |
| 4,116,985 | 9/1978 | Salmond . |
| 4,388,243 | 6/1983 | Nishikawa et al. . |
| 5,145,846 | 9/1992 | Baggiolini et al. ............... 514/167 |
| 5,194,431 | 3/1993 | DeLuca et al. . |
| 5,218,109 | 6/1993 | Tsuji et al. ........................ 540/4 |
| 5,342,833 | 8/1994 | Doran et al. ...................... 514/167 |
| 5,352,781 | 10/1994 | Yiannikouros et al. ............ 540/4 |
| 5,393,900 | 2/1995 | Doran et al. ...................... 552/505 |

OTHER PUBLICATIONS

J. Y. Zhou, et al. Pro. Natl. Acad. Sci. USA 87: pp. 3929–3932 (1990).

Calverley et al., Vitamin D in Antitumor Steroids by R.T. Blickenstaff 1992, pp. 193–270.

Primary Examiner—Deborah C. Lambkin
Attorney, Agent, or Firm—George W. Johnston; Patricia S. Rocha-Tramaloni; Robert A. Silverman

[57] ABSTRACT

A process for preparing 1,25-dihydroxy-16-ene-23-yne cholecalciferol.

5 Claims, No Drawings

PROCESS FOR THE PREPARATION OF 1,25-DIHYDROXY-16-ENE-23-YNE-CHOLECALCIFEROL

This application is a continuation of Ser. No. 08/356,942 filed Dec. 15, 1994, abandoned, which is a continuation of Ser. No. 08/192,665 filed Feb. 7, 1994 both abandoned.

BACKGROUND OF THE INVENTION 1,25-dihydroxy-16-ene-23-yne cholecalciferol is a known compound useful in the treatment of leukemia. U.S. Pat. No. 5,145,846, issued Sep. 8, 1992.

The known methods of preparing 1,25-dihydroxy-16-ene-23-yne cholecalciferol include that set forth in U.S. Pat. No. 5,145,846.

BRIEF SUMMARY OF THE INVENTION

The invention relates to a process for the preparation of the compound 1,25-dihydroxy-16-ene-23-yne cholecalciferol, represented by the formula:

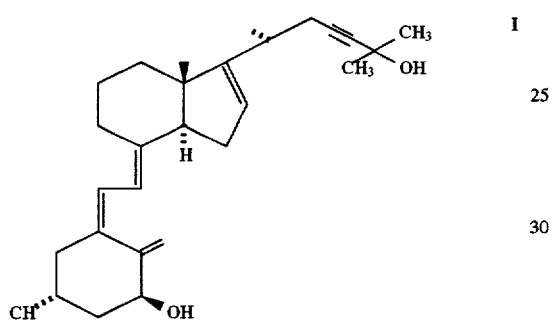

I which process comprises a) reacting a compound of formula II

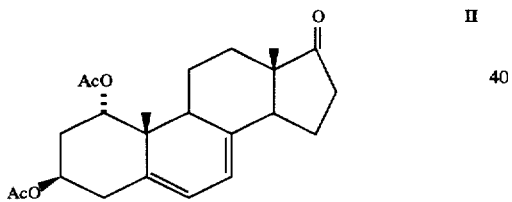

II wherein Ac is acetyl, to form a compound of formula III

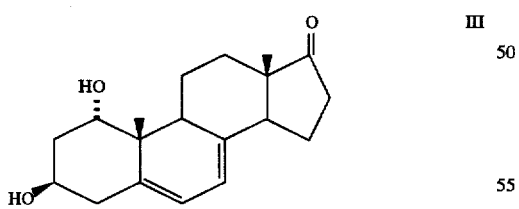

III b) reacting a compound of formula III to form a compound of formula IV

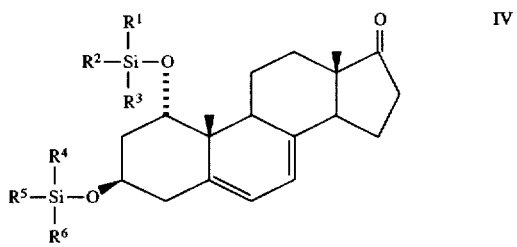

IV wherein $R^1$, $R^2$ and $R^3$ are independently $C_1$–$C_2$ alkyl, and $R^4$, $R^5$ and $R^6$ are independently $C_1$–$C_6$ alkyl; provided that one of $R^4$, $R^5$ and $R^6$ is tert-butyl or thexyl, c) reacting a compound of formula IV, to form a compound of formula V

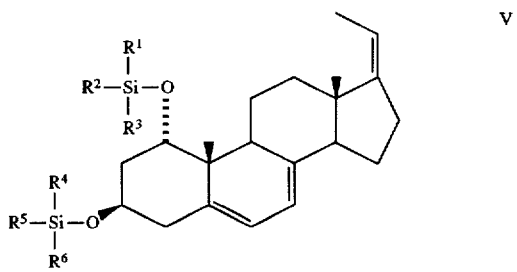

V wherein $R^1$, $R^2$, $R^3$, $R^4$, $R^5$ and $R^6$ are as described above, d) reacting a compound of formula V with a compound of formula VI,

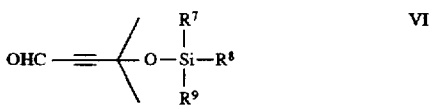

VI wherein $R^7$, $R^8$ and $R^9$ are independently $C_1$–$C_6$ alkyl; provided that one of $R^7$, $R^8$ and $R^9$ is tert-butyl or thexyl, to form a compound of formula VII

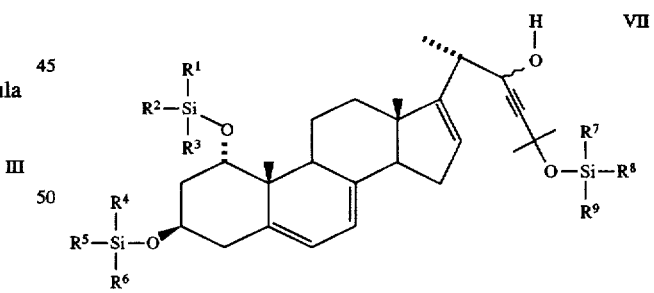

VII wherein $R^1$, $R^2$, $R^3$, $R^4$, $R^5$, $R^6$, $R^7$, $R^8$ and $R^9$ are as described above, e) reacting a compound of formula VII to form a compound of formula VIII

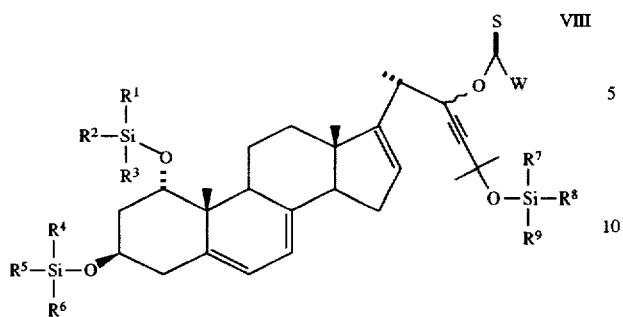

wherein $R^1$, $R^2$, $R^3$, $R^4$, $R^5$, $R^6$, $R^7$, $R^8$ and $R^9$ are as described above, W is

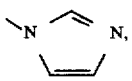

—NHPh, —OPh, —N(CH$_3$)$_2$, or —SCH$_3$, and Ph is phenyl, f) reacting a compound of formula VIII to form a compound of formula IX

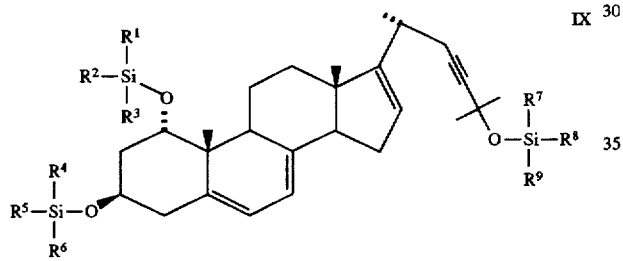

wherein $R^1$, $R^2$, $R^3$, $R^4$, $R^5$, $R^6$, $R^7$, $R^8$ and $R^9$ are as described above, g) reacting a compound of formula IX to form a compound of formula X

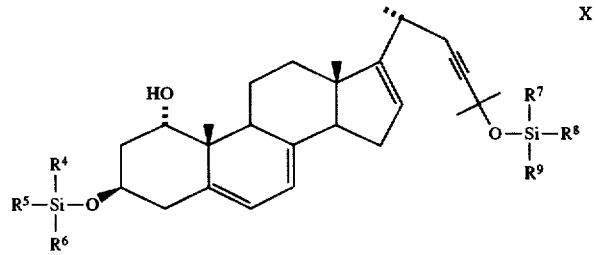

wherein $R^4$, $R^5$, $R^6$, $R^7$, $R^8$ and $R^9$ are as described above, h) reacting a compound of formula X to form a compound of formula XI

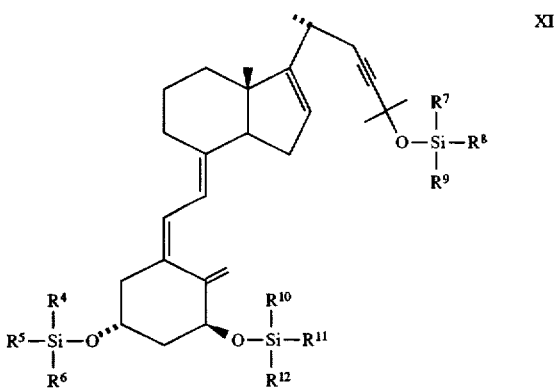

wherein $R^4$, $R^5$, $R^6$, $R^7$, $R^8$ and $R^9$ are as described above, and $R^{10}$, $R^{11}$ and $R^{12}$ are independently $C_1$–$C_6$ alkyl or aryl; provided that one of $R^{10}$, $R^{11}$ or $R^{12}$ is tert-butyl or thexyl, i) reacting a compound of formula XI to form the compound of formula I.

DETAILED DESCRIPTION OF THE INVENTION

In the formulas represented herein, when substituents are illustrated as joined to the nucleus by a solid line (

◂

), it indicates that the substituent is above the plane of the molecule, a broken line (

...

), indicates that the substituent is below the plane of the molecule, and a wavy line (

∼

), indicates that the substituent is either above the plane of the molecule or below the plane of the molecule.

The term "alkyl", alone or in combination, denotes a straight-chain or branched chain alkyl group containing 1 to 10, preferably 1 to 6, carbon atoms. Alternatively, the number of carbon atoms is an alkyl group is designated herein as in "$C_1$–$C_6$ alkyl" which denotes a straight or branched-chain alkyl group containing 1 to 6 carbon atoms. The term "aryl" denotes phenyl or naphthyl, preferably phenyl. The term "halogen" denotes bromine and chlorine, preferably chlorine.

The invention relates to a process for the preparation of the compound 1,25-dihydroxy-16-ene-23-yne cholecalciferol, represented by the formula:

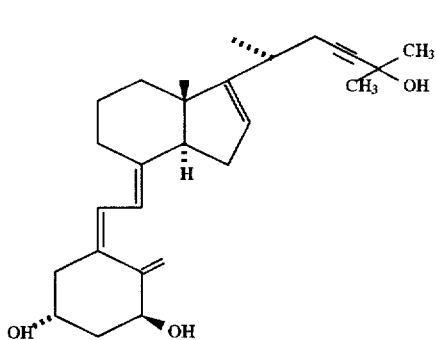

which process comprises
a) reacting a compound of formula II

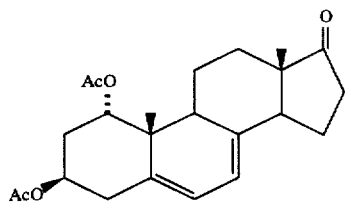

wherein Ac is acetyl, to form a compound of formula III

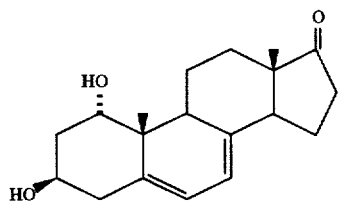

b) reacting a compound of formula III to form a compound of formula IV

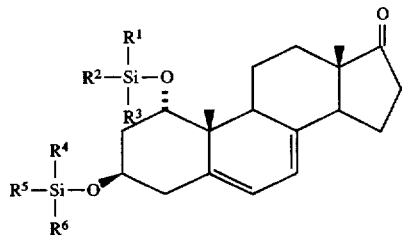

wherein $R^1$, $R^2$ and $R^3$ are independently $C_1$–$C_2$ alkyl, and $R^4$, $R^5$ and $R^6$ are independently $C_1$–$C_6$ alkyl; provided that one of $R^4$, $R^5$ and $R^6$ is tert-butyl or thexyl, c) reacting a compound of formula IV, to form a compound of formula V

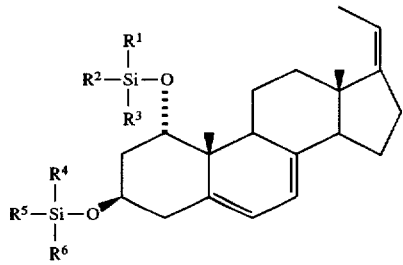

wherein $R^1$, $R^2$, $R^3$, $R^4$, $R^5$ and $R^6$ are as described above, d) reacting a compound of formula V with a compound of formula VI,

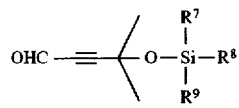

wherein $R^7$, $R^8$ and $R^9$ are independently $C_1$–$C_6$ alkyl; provided that one of $R^7$, $R^8$ and $R^9$ is tert-butyl or thexyl, to form a compound of formula VII

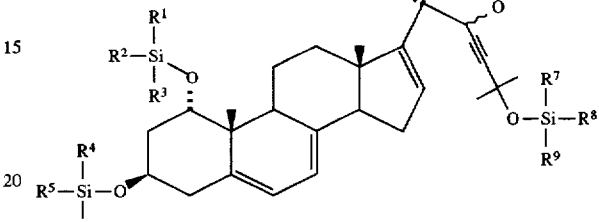

wherein $R^1$, $R^2$, $R^3$, $R^4$, $R^5$, $R^6$, $R^7$, $R^8$ and $R^9$ are as described above, e) reacting a compound of formula VII to form a compound of formula VIII

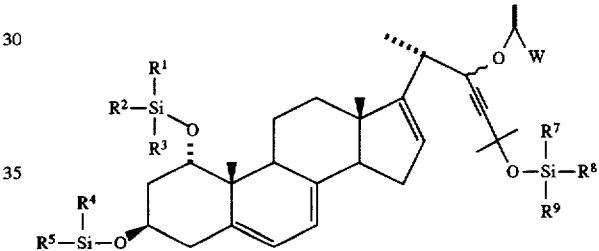

wherein $R^1$, $R^2$, $R^3$, $R^4$, $R^5$, $R^6$, $R^7$, $R^8$ and $R^9$ are as described above,
W is

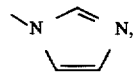

—NHPh, —OPh, —N(CH$_3$)$_2$, or —SCH$_3$ and Ph is phenyl, f) reacting a compound of formula VIII to form a compound of formula IX

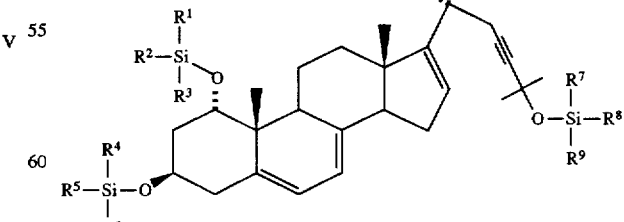

wherein $R^1$, $R^2$, $R^3$, $R^4$, $R^5$, $R^6$, $R^7$, $R^8$ and $R^9$ are as described above, g) reacting a compound of formula IX to form a compound of formula X

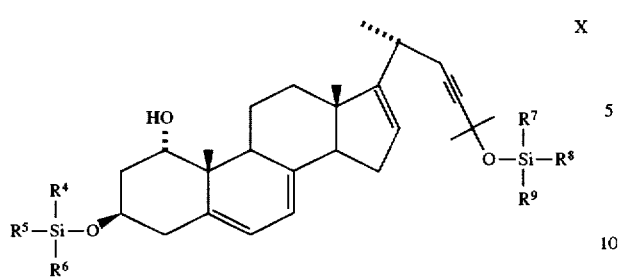

wherein $R^4$, $R^5$, $R^6$, $R^7$, $R^8$ and $R^9$ are as described above.

h) reacting a compound of formula X to form a compound of formula XI

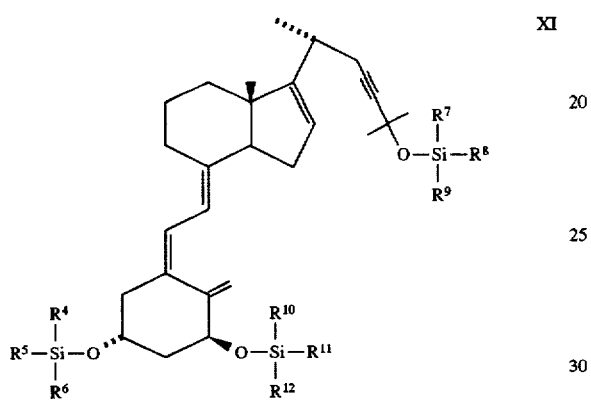

wherein $R^4$, $R^5$, $R^6$, $R^7$, $R^8$ and $R^9$ are as described above, and $R^{10}$, $R^{11}$ and $R^{12}$ are independently $C_1$-$C_6$ alkyl or aryl; provided that one of $R^{10}$, $R^{11}$ or $R^{12}$ is tert-butyl or thexyl.

i) reacting a compound of formula XI to form the compound of formula I.

SCHEME I

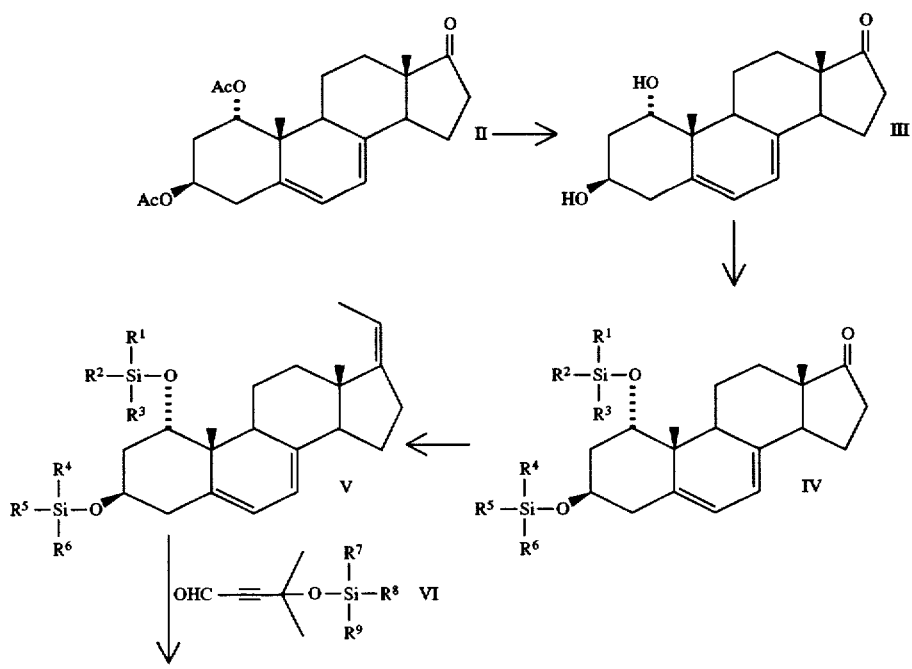

SCHEME I (-continued)

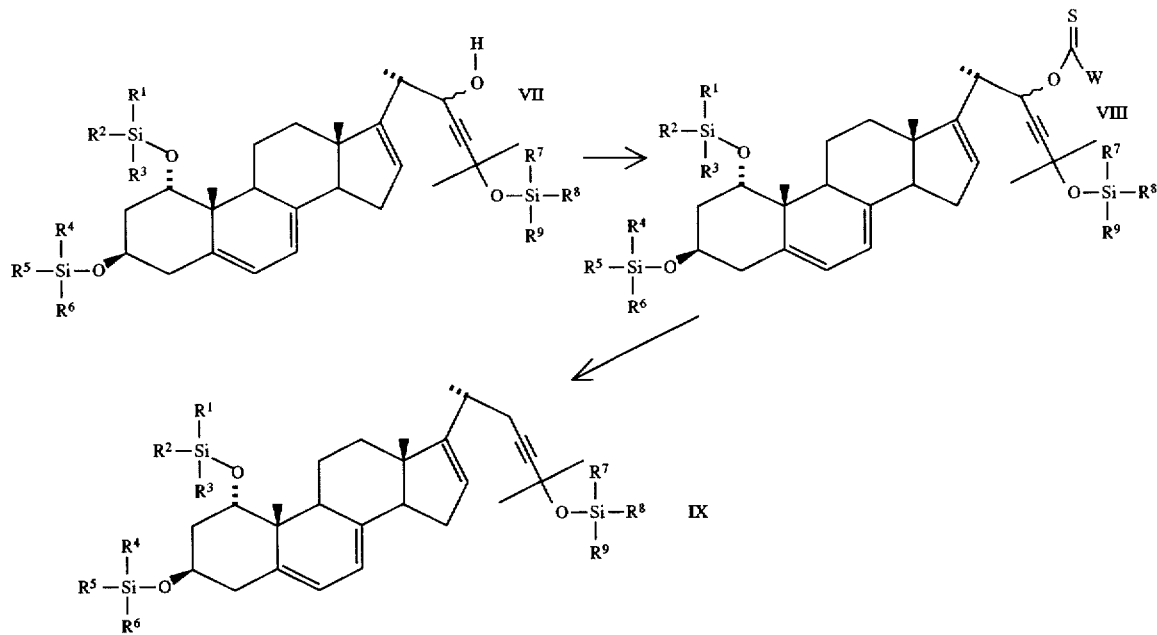

As set forth in Scheme I, a compound of formula II is treated with a base such as sodium methoxide in a protic solvent, preferably methanol, to form a compound of formula III.

A compound of formula III is treated with, for example, trialkylsilyl chloride such as preferably chlorodimethylthexylsilane, followed by triethylsilyl chloride in an aprotic solvent, such as methylene chloride, dimethylformamide, preferably methylene chloride, in the presence of a base such as imidazole, to form a compound of formula IV.

A compound of formula IV is reacted with ethylenetriphenylphosphorane in an aprotic solvent, such as toluene, tetrahydrofuran, ether and the like, preferably toluene, to form a compound of formula V.

A corresponding compound of formula V is reacted with a compound of formula VI in an aprotic solvent, such as hexane, dichloromethane, toluene, and the like, preferably hexane, in the presence of a Lewis acid, such as dimethylaluminum chloride, preferably in the temperature range of from 0° to −78° C., preferably from −40° to −78° C., to form the corresponding compound of formula VII.

The compound of formula VII is treated with, for example, 1,1'-thiocarbonyldiimidazole, phenyl chlorothionoformate, dimethylthiocarbonyl chloride, carbon disulfide, or preferably phenyl isothiocyanate in an aprotic solvent, such as, dimethylformamide, tetrahydrofuran and the like, preferably tetrahydrofuran in the presence of a base such as sodium hydride, diazabicycloundecene and the like, to form a compound of formula VIII.

A compound of formula VIII is treated with alkyltin hydride, such as, preferably tributyltin hydride and a radical initiator, such as 2,2'-azobis(2-methylpropionitrile), benzoyl peroxide, preferably 2,2'-azobis(2-methylpropionitrile), in an aprotic solvent, such as hexane, toluene, or cyclohexane, preferably hexane, at, preferably, reflux temperature to form a compound of formula IX.

SCHEME II

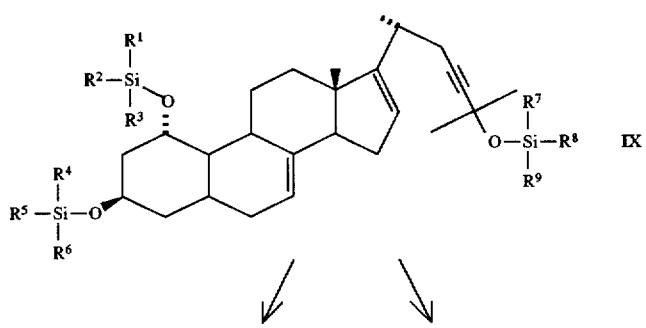

-continued
SCHEME II

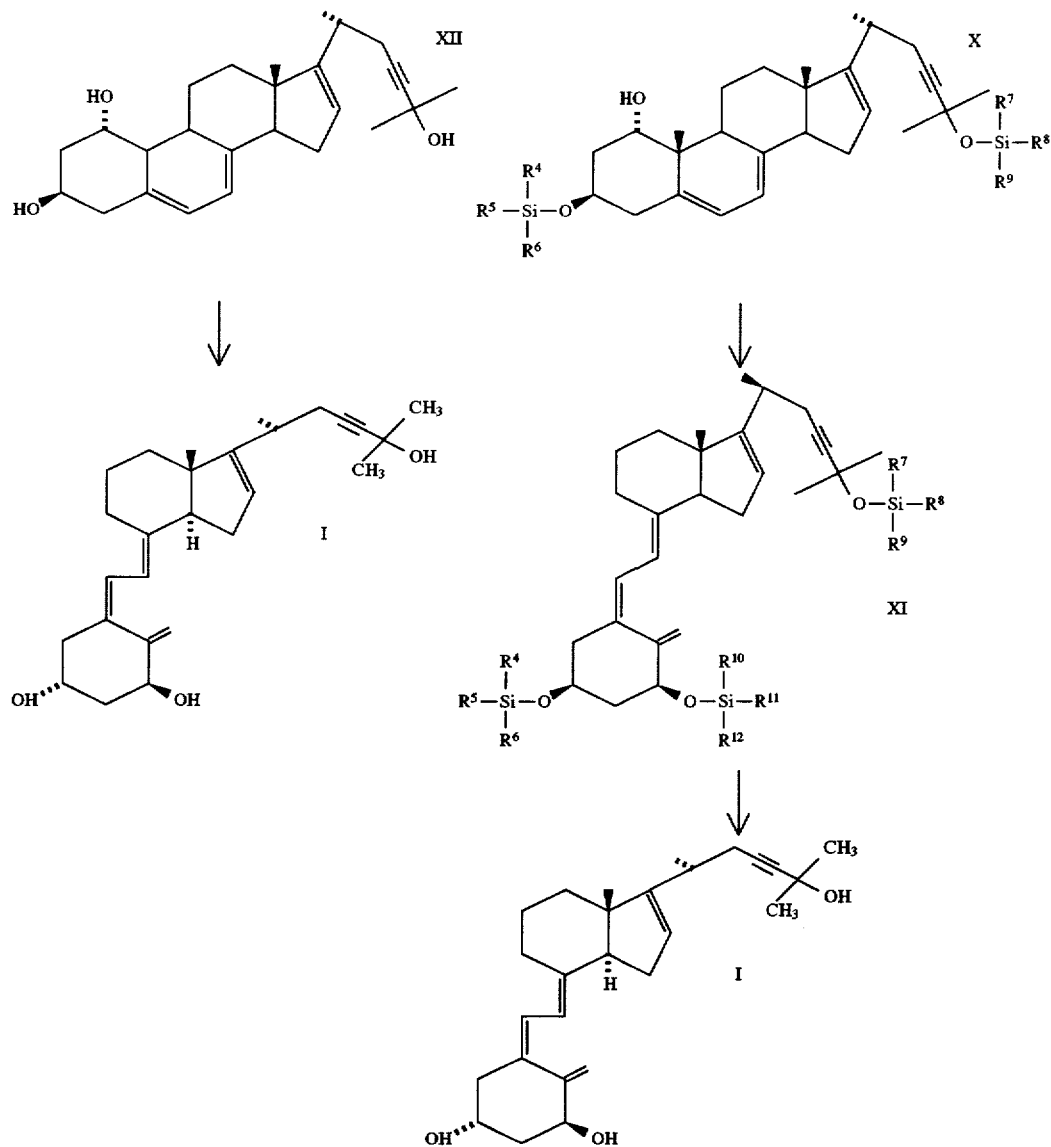

As set forth in Scheme II, a compound of formula IX is treated with a fluoride salt, such as cesium fluoride, tetraalkylammonium fluoride, preferably tetrabutylammonium fluoride in preferably tetrahydrofuran at a temperature in the range of from −20° C. to 50° C., preferably in the range of 0°–25° C. to form a compound of formula X.

The compound of formula X is irradiated in an inert solvent, such as tert-butyl methyl ether, diethyl ether, tetrahydrofuran, preferbly tert-butyl methyl ether preferably with a medium pressure mercury lamp in the presence of a substance that acts as a filter to block 290–320 nm light, such as, preferably ethyl 4-dimethylaminobenzoate and subsequently irradiated through a uranium filter in the presence of anthracene preferably 9-acetylanthracene as a sensitizer to isomerization to form a photolysis product.

Subsequently, the photolysis product is subjected to thermal isomerization in an organic solvent, at a temperature preferably in the range of 30°–120° C. The product of the above stated thermal isomerization is treated with a compound of the formula

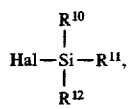

wherein Hal is halogen, and $R^{10}$, $R^{11}$ and $R^{12}$ are as described above, such as chlorordimethylthexylsilane in an aprotic solvent, such as methylene chloride in the presence of a base such as imidazole, to form a compound of formula XI.

The compound of formula XI is treated with a fluoride salt, such as tetrabutylammonium fluoride in preferably tetrahydrofuran to form a compound of formula I.

Alternatively, a compound of formula IX is treated with a fluoride salt, such as cesium fluoride, tetraalkylammonium fluoride, preferably tetrabutylammonium fluoride in preferably tetrahydrofuran at a temperature in the range of from −20° C. to 80° C., preferably in the range of 20°–50° C. to form a compound of formula XII.

The compound of formula XII is irradiated in an inert solvent, such as tert-butyl methyl ether, diethyl ether, tetrahydrofuran, ethanol, methanol, preferably a mixture of tert-butyl methyl ether and methanol, preferably with a medium pressure mercury lamp in the presence of a substance that acts as a filter to block 290–320 nm light, such as, preferably ethyl 4-dimethylaminobenzoate and subsequently irradiated through a uranium filter in the presence of anthracene preferably 9-acetylanthracene as a sensitizer to isomerization to form a photolysis product.

Subsequently, the photolysis product is subjected to thermal isomerization in an organic solvent, at a temperature preferably in the range of 30°–120° C. to form a compound of formula I.

The examples which follow further illustrate the invention.

EXAMPLE 1

(1α,3β)-1,3-Dihydroxyandrosta-5,7-dien-17-one

A 3-L three-necked flask equipped with a mechanical stirrer was charged with 114.5 g (296 mmol) of (1α,3β)-1, 3-bis (acetyloxy)androsta-5,7-dien-17-one, a known compound, 586 mL of methanol, and 29 mL of 25% sodium methoxide in methanol. After stirring at room temperature for 20 hr, the reaction was quenched by the addition of 7.4 mL of acetic acid. Then, 880 mL of water was added dropwise over 1 h, and the mixture was stirred for another hour and then stored in a refrigerator overnight. The precipitate was filtered and washed with 3×200 mL of methanol:water (1:2). The brown solid was dried by suction for 1 hr and then under high vacuum to afford 60.1 g of (1α,3β) -1,3-dihydroxyandrosta-5,7-dien-17-one.

EXAMPLE 2

(1α,3β)-3-[[Dimethyl(1,1,2-trimethylpropyl)silyl] oxy]-1-[(triethylsilyl)oxy]androsta-5,7-dien-17-one A 3-L three-necked flask equipped with a mechanical stirrer, addition funnel, and Ar-inlet tube was charged with 60.1 g (199 mmol) of (1α,3β)-1,3-dihydroxyandrosta-5,7-dien-17-one, 40.7 g (598 mmol) of imidazole, and 400 mL of dichloromethane. After cooling with an ice-water bath for 5 min., 50.7 mL (257 mmol) of thexyldimethylsilyl chloride was added over 12 min. The cold bath was removed, and the mixture was stirred at room temperature for 5 hr. After cooling again with an ice-water bath. 36.8 mL (219 mmol) of triethylsilyl chloride was added over 10 min. After stirring at room temperature overnight, 220 mL of hexane was added. After 15 min, the precipitate was removed by filtration and washed with 2×120 mL of hexane. The combined filtrate and washes were concentrated, and the residual hexane was removed by co-evaporation with 120 mL of methanol, and the suspension was stirred for 2 hr in order to obtain a powdery material. After the suspension was stored in a refrigerator overnight, the precipitate was filtered and washed with 2×160 mL of 95% methanol. Drying under high vacuum afforded 96.8 g of (1α,3β)-3-[[dimethyl(1,1,2-trimethylpropyl)silyl]oxy]-1-[(triethylsilyl)oxy]androsta-5, 7-dien-17-one as a beige solid.

EXAMPLE 3

(1α,3β,17Z)-Dimethyl[[1-[(triethylsilyl)oxy]pregna-5,7,17(20)-trien-3-yl]oxy](1,1,2-trimethylpropyl) silane A 2-L three-necked flask equipped with a mechanical stirrer and an Ar-inlet tube was charged with 90.0 g (242 mmol) of ethyl triphenylphosphonium bromide and 480 mL of toluene. To the suspension, 27.2g (242 mmol) of potassium t-butoxide was added. After stirring at room temperature for 2 hr, the orange-red mixture was cooled with an ice-water bath. Then, 96.8 g (173 mmol) of (1α,3β)-3-[ [dimethyl(1,1,2-trimethylpropyl)silyl]oxy]-1-[(triethylsilyl) oxy]androsta-5,7-dien-17-one was added with the aid of 30 mL of toluene. The mixture was stirred at room temperature overnight, and the reaction was quenched by the addition of 3.96 mL of acetic acid (69 mmol). After stirring for an additional hour, the suspension was filtered through a Celite pad. The filter cake was washed with 2×130 mL of toluene. The combined filtrate and washes were concentrated, and the residual toluene was removed by co-evaporation with 180 mL of methanol followed by drying under high vacuum. The residue was then dissolved in a mixture of 350 mL of hexane and 350 mL of 95% methanol. The hexane layer was washed with 180 mL of 95% methanol. The combined methanol layers were extracted with 2×150 mL of hexane. The combined hexane solutions were dried over sodium sulfate (Na$_2$SO$_4$), and concentrated. The residual hexane was removed by co-evaporation with 30 mL of methanol. The resulting solid residue was suspended in 175 mL of methanol, and the suspension was stirred for 1 hr to obtain a powdery material. After the suspension was stored in a refrigerator overnight, the precipitate was filtered and washed with 2×175 mL of 95% methanol. Drying under high vacuum gave 91.1 g (92.9% yield) of (1α,3β,17Z)-dimethyl [[1-[(triethylsilyl)oxy]pregna-5,7,17(20)-trien-3-yl]oxy](1, 1,2-trimethylpropyl)silane as an off-white solid.

EXAMPLE 4

(1α,3β)-25-[[(1,1-Dimethylethyl)dimethylsilyl]oxy]-3-[[dimethyl(1,1,2-trimethylpropyl)silyl]oxy]-1-[(triethylsilyl)oxy]cholesta-5,7,16-trien-23-yn-22-ol A 3-L three-necked flask equipped with a mechanical stirrer, thermometer, addition funnel, and Ar-inlet tube was charged with 91.9 g (160 mmol) of (1α,3β,17Z)-dimethyl[ [1-[(triethylsilyl)oxy]pregna-5,7,17(20)-trien-3-yl]oxy](1,1, 2-trimethylpropyl)silane, 62.8 mL (240 mmol) of 4-[[(1,1-dimethylethyl)dimethylsilyl]oxy-4-methyl-2-pentynal, and 480 mL of hexane. After cooling to −75° C., 480 mL (480 mmol) of a 1M dimethylaluminum chloride solution in hexane was added over 1 hr. After stirring at −75° C. for 1.5 hr., 66.9 mL (480 mmol) of triethylamine was added followed by 147 mL of ammonium hydroxide over 5 min. After 5 min, the cold-bath was removed, and the mixture was stirred for 2 hr (Gas evolved). Then, 147 g of powder Na$_2$SO$_4$ was added, and the stirring was continued for 30 min. The solid was removed by filtration and washed with a total of 720 mL of hexane. The combined hexane solutions were washed with 480 mL of 95% methanol. The methanol layer was extracted with 240 mL of hexane. The combined hexane solutions were dried over Na$_2$SO$_4$ and concentrated. The residue was then dried under high vacuum overnight to give 153 g (overweight) of crude (1α,3β)-25-[[(1,1-dimethylethyl)dimethylsilyl]oxy]-3-[[dimethyl(1,1,2-trimethylpropyl)silyl]oxy]-1-[(triethylsilyl)oxy]cholesta-5, 7,16-trien-23-yn-22-ol as a brown viscous oil.

EXAMPLE 5

(1α,3β)-Phenylcarbamothioic Acid O-[25-[[(1,1-dimethylethyl) dimethylsilyl]oxy]-3-[[dimethyl(1,1, 2-trimethylpropyl)silyl]oxy]-1-[(triethylsilyl)oxy] cholesta-5,7,16-trien-23-yn-22-yl] ester A 2-L three-necked flask equipped with a mechanical stirrer, thermometer, addition funnel, and Ar-inlet tube was charged with 19.2 g (480 mmol) of NaH (60% oil dispersion) and 160 mL of tetrahydrofuran. After cooling with an ice-water bath, a solution of 153 g (160 mmol; theoretical) of crude (1α,3β)-25-[[(1,1-dimethylethyl) dimethylsilyl]oxy]-3-[[dimethyl (1,1,2-trimethylpropyl) silyl]oxy]-1-[(triethylsilyl)oxy]cholesta-5,7,16-trien-23-yn-22-ol in 480 mL of tetrahydrofuran was added dropwise over 45 min. After stirring for 1.5 hr with ice-water cooling, 38.3 mL (320 mmol) of phenyl isothiocyanate was added. After 30 min, the cold-bath was removed, and the mixture was stirred for 45 min. After cooling with an ice-water bath for 5 min., 18.3 mL (320 mmol) of acetic acid was added dropwise over 5 min. After 5 min, 640 mL of water and 320 mL of ethyl acetate (EtOAc) were added. The aqueous layer was extracted with 160 mL of EtOAc. The combined organic solutions were dried over $Na_2SO_4$ and concentrated to dryness. The residue was dissolved in a mixture of 640 mL of hexane and 640 mL of 95% methanol. The hexane layer was washed with 320 mL of 95% methanol. The combined methanol layers were extracted with 320 mL of hexane. The combined hexane layers were dried over $Na_2SO_4$ and concentrated to dryness. The residue was dried under high vacuum overnight to give 186 g (overweight) of crude (1α,3β)-phenylcarbamothioic acid O-[25-[[(1,1-dimethylethyl)dimethylsilyl]oxy]-3-[[dimethyl(1,1,2-trimethylpropyl)silyl]oxy]-1-[(triethylsilyl)oxy]cholesta-5,7,16-trien-23-yn-22-yl] ester as a dark brown viscous oil.

EXAMPLE 6

(1α,3β)-[[25-[[(1,1-Dimethylethyl)dimethylsilyl] oxy]-3-[[dimethyl (1,1,2-trimethylpropyl)silyl]oxy] cholesta-5,7,16-trien-23-yn-1-yl]oxy]triethylsilane A 2-L flask equipped with a magnetic stirrer, reflux condenser, and Ar-inlet tube was charged with 186 g (160 mmol; theoretical) of crude (1α,3β)-phenylcarbamothioic acid O-[25-[[(1,1-dimethylethyl) dimethylsilyl]oxy]-3-[ [dimethyl(1,1,2-trimethylpropyl)silyl]oxy]-1-[(triethylsilyl) oxy]cholesta-5,7,16-trien-23-yn-22-yl] ester, 172 mL (640 mmol) of tributyltin hydride, and 480 mL of hexane. The mixture was heated to about 50° C., and 15.8 g (96 mmol) of 2'2-azobis(2-methylpropionitrile) (AIBN) was added. The mixture was refluxed for 1.5 hr. After cooling, the hexane was removed by evaporation. The residual hexane was removed by co-evaporation with 2×200 mL of methanol. The residue was mixed with 1 L of methanol, and the mixture was stirred vigorously for 10 min and let stand for 30 min. Then the upper methanol layer was removed by decantation and discarded. The methanol treatment was repeated two more times. The residue was mixed with 500 mL of acetone, and the mixture was diluted with 750 mL of methanol with stirring over 30 min. After standing for 30 min, the upper layer was removed by decantation and discarded. This procedure was repeated two more times. In the last treatment, the crude product was filtered and washed with 250 mL of methanol-acetone (3:2). After being dried by suction for 15 min, the solid was again suspended in 500 mL of acetone. After stirring for 15 min, 750 mL of methanol was added dropwise over 30 min, and the mixture was stirred at room temperature overnight. The pale yellow solid was filtered and washed with 250 mL of methanol-acetone (3:2). After being dried by suction for 15 min, the solid was again suspended in 500 mL of acetone. After stirring for 15 min., 500 mL of methanol was added dropwise over 30 min, and the mixture was stirred at room temperature overnight. The pale yellow solid was filtered and washed with 250 mL of methanol-acetone (3:2). Drying under high vacuum gave 63.6 g (1α,3β)-[[25-[[(1,1-dimethylethyl)dimethylsilyl]oxy] -3-[[dimethyl(1,1,2-trimethylpropyl)silyl]oxy]cholesta-5,7, 16-trien-23-yn-1-yl]oxy]triethylsilane as a pale yellow solid.

EXAMPLE 7

(1α,3β)-25-[[(1,1-Dimethylethyl) dimethylsilyl]oxy] -3-[[dimethyl(1,1,2-trimethylpropyl)silyl]oxy] cholesta-5,7,16-trien-23-yn-1-ol A 100-mL flask equipped with a magnetic stirrer and Ar-inlet tube was charged with 15.0 g (19.2 mmol) of (1α,3β)-25-[[(1,1-dimethylethyl)dimethylsilyl]oxy]-3-[ [dimethyl(1,1,2-trimethylpropyl)silyl]oxy]cholesta-5,7,16-trien-23-yn-1-yl]oxy]triethylsilane and 19.2 mL of tetrahydrofuran. To this solution was added 19.2 mL (19.2 mmol) of 1M tetrabutylammonium fluoride ($Bu_4NF$) in tetrahydrofuran. After stirring at room temperature for 2.5 hr, the mixture was diluted with 100 mL of hexane and 50 mL of water. The aqueous layer was extracted with 50 mL of hexane. The combined hexane layers were dried over sodium sulfate and concentrated to dryness. The residue was then partitioned by gentle swirling between 100 mL of hexane and 100 mL of 95% methanol. The hexane layer was washed by gentle swirling with 50 mL of 95% methanol. The combined methanol layers were back-extracted with 50 mL of hexane by gentle swirling. The combined hexane layers were concentrated and dried under high vacuum overnight to give 14.5 g (overweight) of a tan oil. The crude material was immediately used in the next step.

EXAMPLE 8

[[(1α,3β,5Z,7E)-25-[[(1,1-Dimethylethyl) dimethylsilyl]oxy]-9,10-secocholesta-5,7,10(19),16-tetraen-23-yne-1,3-diyl]bis(oxy)bis[dimethyl(1,1,2-trimethylpropyl)silane]

A 2-L photo reaction vessel (Ace Glass, #7851-17) equipped with a quartz immersion well, thermometer, Ar-inlet tube, and mechanical stirrer was charged with 14.5 g (19.2 mmol; theoretical) of crude (1α,3β)-25-[[(1,1-dimethylethyl)dimethylsilyl]oxy]-3-[[dimethyl(1,1,2-trimethylpropyl)silyl]oxy]cholesta-5,7,16-trien-23-yn-1-ol; 1.2 g of ethyl 4-dimethylaminobenzoate, and 1.7 L of tert-butyl methyl ether (t-BuOMe). After cooling to –20° C., the solution was irradiated with a 450 W medium pressure Hg lamp through the well which was cooled by circulation of 10% aqueous methanol (making sure there is no absorption at 254 nm) at 15° C. During the photolysis, the arc housing was constantly purged with a slow current of nitrogen. After 7 hr of irradiation at –5° to –25° C., a uranium filter was inserted in the arc housing and then 60 mg of 9-acetylanthracene was added to the solution. After 1.5 hr of irraditation through the filter at that temperature, the solution was allowed to warm to room temperature overnight. The solution was concentrated to about 500 mL, and refluxed for 5 hr. After cooling to room temperature, the solvent was removed. The residue was dissolved in 100 ml of dichloromethane, and the solution was transferred to a 500 mL flask equipped with a magnetic stirrer and Ar-inlet tube. After cooling with an ice-water bath, 6.53 g (96 mmol) of imidazole was added followed by 9.44 mL (48 mmol) of thexyldimethylsilyl chloride. After stirring at room temperature overnight, the mixture was diluted with 100 mL of hexane. After 10 min, the precipitate was filtered through a Celite pad and washed with 200 mL of hexane. The combined filtrate and washes were concentrated to dryness.

Then, the residue was partitioned between 100 mL of hexane and 100 mL of 95% methanol. The hexane layer was concentrated to dryness. The residue was then purified by chromatography on 250 g of silica gel-60 eluting with 1 L of hexane, with 1 L of 10% $CH_2Cl_2$ in hexane, and with 1.5 L of 15% $CH_2Cl_2$ in hexane. The desired fractions were combined and concentrated. The residue was dried under high vacuum for 2 h to give 7.45 g of [[(1α,3β,5Z,7E)-25-[[(1,1-dimethylethyl)dimethylsilyl]oxy]-9,10-secocholesta-5,7,10(19),16-tetraen-23-yne-1,3-diyl]bis (oxy)bis[dimethyl (1,1,2-trimethylpropyl)silane] as a clear oil.

EXAMPLE 9

(1α,3β,5Z,7E)-9,10-Secocholesta-5,7,10(19), 16-tetraen-23-yne-1,3,25-triol

A 250-mL flask equipped with a magnetic stirrer, Ar-inlet tube, and reflux condenser was charged with 7.45 g (9.2 mmol) of [[(1α,3β,5Z,7E)-25-[[(1,1-dimethylethyl) dimethylsilyl]oxy]-9,10-secocholesta-5,7,10(19),16-tetraen-23-yne-1,3-diyl]bis (oxy)bis[dimethyl(1,1,2-trimethylpropyl)silane] and 92 mL (92 mmol) of 1M $Bu_4NF$ in tetrahydrofuran. The mixture was stirred at 45° C. overnight. After cooling to room temperature, the mixture was diluted with 100 mL of ethyl acetate and 100 mL of water. The aqueous layer was extracted with 2×50 mL of ethyl acetate. Each organic layer was washed with 50 mL each of water. The combined organic layers were dried over sodium sulfate and concentrated to dryness. The residue was partitioned between 100 mL of hexane and 75 mL of 90% methanol. The hexane layer was extracted with 25 mL of 90% methanol. The combined methanol layers were washed with 50 mL of hexane, and the hexane layer was extracted with 10 mL of 90% methanol. The combined methanol layers were concentrated and dried under high vacuum at room temperature to give 5.9 g of a semi-solid. This was dissolved in 40 mL of warm methanol and diluted with 20 mL of water. After the solution was cooled to room temperature, a seed crystal was added, and the mixture was stored in a refrigerator for 4 days. The precipitate was filtered and washed with 50 mL of a mixture of methanol :water (3:2) and then with 40 mL of hexane. Drying under high vacuum at room temperature for 31 h gave 2.03 g (53.7 % yield) of (1α,3β,5Z,7E)-9,10-secocholesta-5,7,10(19),16-tetraen-23-yne-1,3,25-triol as a white solid: mp 80°-85° C.

EXAMPLE 10

(1α,3β)-Cholesta-5,7,16-trien-23-yne-1,3,25-triol

A mixture of 20.7 g (26.5 mmol) of (1α,3β)-[[25-[[(1,1-dimethylethyl)dimethylsilyl]oxy]-3-[[dimethyl(1,1,2-trimethylpropyl)silyl]oxy]cholesta-5,7,16-trien-23-yn-1-yl] oxy]triethylsilane and 265 mL (265 mmol) of 1M $Bu_4NF$ in tetrahydrofuran was stirred at 30°-35° C. for 40 hr. After cooling to room temperature, 265 mL of EtOAc and 265 mL of water were added. The aqueous layer was extracted with 2×125 mL of EtOAc. The combined EtOAc solutions were concentrated to dryness. The residue was suspended in 130 mL of hexane and 130 mL of water, and the mixture was stirred for 30 min prior to filtration. The solid was washed with 130 mL of water and then with 130 mL of hexane. After being dried by suction, the solid was dissolved in 90 mL of hot methanol. After the solution was diluted with 45 mL of water and cooled to room temperature, the mixture was stored in a refrigerator overnight. The precipitate was filtered and washed with 100 mL of methanol-water (2:1). Drying at room temperature under high vacuum for 24 hr gave 9.37 g of (1α,3β)-cholesta-5,7,16-trien-23-yne-1,3,25-triol

EXAMPLE 11

(1α,3β,5Z,7E)-9,10-Secocholesta-5,7,10(19),16-tetraen-23-yne-1,3,25-triol

A 2-L photoreactor was charged with 10 g (24.4 mmol) of (1α,3β)-cholesta-5,7,16-trien-23-yne-1,3,25-triol, 1 g of ethyl 4-dimethylaminobenzoate, 1.45 L of methanol, and 250 mL of tert-butyl methyl ether. After cooling to −10° C., the solution was irradiated with a 450 W medium pressure Hg lamp at −10° to −30° C. for 7.5 hr. A uranium filter was inserted to the arc housing, and 50 mg of 9-acetylanthracene in 2 mL of tert-butyl methyl ether was added. The mixture was irradiated with the same lamp through the filter at −10° to −30° C. for 1.5 hr. The mixture was allowed to warm to from temperature overnight. The solution was concentrated to about 1 L, and then refluxed for 4 hr. The mixture was allowed to cool to room temperature overnight, and concentrated to dryness. The residue was purified repeatedly by chromatography on silica gel, eluting with 60% EtOAc in hexane. The desired fractions were combined and concentrated to dryness. The residue was then recrystallized from aqueous methanol to afford (1α,3β,5Z,7E)-9,10-secocholesta-5,7,10(19),16-tetraen-23-yne-1,3,25-triol.

I claim:

1. The compound (1α,3β)-25-[[(1,1-dimethylethyl) dimethylsilyl]oxy]-3-[[dimethyl(1,1,2-trimethylpropyl) silyl]oxy-1-[(triethylsilyl)oxy]cholesta-5,7,16-trien-23-yn-22-ol.

2. The compound (1α,3β)-phenylcarbamothioic acid O-[25-[[(1,1-dimethylethyl)dimethylsilyl]oxy]-3-[[dimethyl(1,1,2-trimethylpropyl)silyl]oxy]-1-[[(triethylsilyl) oxy]cholesta-5,7,16-trien-23-yn-22-yl] ester.

3. The compound (1α,3β)-[[25-[[(1,1-dimethylethyl) dimethylsilyl]oxy]-3-[[dimethyl(1,1,2-trimethylpropyl) silyl]oxy]cholesta-5,7,16-trien-23-yn-1-yl]oxy] triethylsilane.

4. The compound (1α,3β)-25-[[(1,1-dimethylethyl) dimethylsilyl]oxy]-3-[[dimethyl(1,1,2-trimethylpropyl) silyl]oxy]cholesta-5,7,16-trien-23-yn-1-ol.

5. The compound [[(1α,3β,5Z,7E)-25-[[(1,1-dimethylethyl)dimethylsilyl]oxy]-9,10-secocholesta-5,7,10 (19) tetraen-23-yne-1,3-diyl]bis(oxy)bis[dimethyl(1,1,2-trimethylpropyl)silane].

* * * * *